(12) United States Patent
Molinari et al.

(10) Patent No.: US 7,138,393 B2
(45) Date of Patent: Nov. 21, 2006

(54) BIOLOGICALLY ACTIVE VASOPRESSIN AGONIST METABOLITES

(75) Inventors: Albert J. Molinari, Pottstown, PA (US); Eugene J. Trybulski, Huntington Valley, PA (US)

(73) Assignee: Wyeth, Madison, NJ (US)

( * ) Notice: Subject to any disclaimer, the term of this patent is extended or adjusted under 35 U.S.C. 154(b) by 35 days.

(21) Appl. No.: 10/320,761

(22) Filed: Dec. 16, 2002

(65) Prior Publication Data

US 2003/0134845 A1    Jul. 17, 2003

Related U.S. Application Data

(63) Continuation-in-part of application No. 09/122,020, filed on Jul. 24, 1998, now Pat. No. 6,511,974.

(51) Int. Cl.
*A61P 13/00* (2006.01)
*A61K 31/55* (2006.01)
*C07D 487/12* (2006.01)

(52) U.S. Cl. ...................... 514/220; 540/561
(58) Field of Classification Search ............... 514/220; 540/561
See application file for complete search history.

(56) References Cited

U.S. PATENT DOCUMENTS

| | | | |
|---|---|---|---|
| 3,326,900 A | 6/1967 | Schmidt et al. | 260/239.3 |
| 4,766,108 A | 8/1988 | Ali | 514/16 |
| 5,055,448 A | 10/1991 | Manning et al. | 514/16 |
| 5,070,187 A | 12/1991 | Gavras et al. | 530/316 |
| 5,420,270 A | 5/1995 | Chandrakumar et al. | 540/488 |
| 5,512,563 A | 4/1996 | Albright et al. | 514/217 |
| 5,516,774 A | 5/1996 | Albright et al. | 514/220 |
| 5,521,173 A | 5/1996 | Venkatesan et al. | 514/220 |
| 5,536,718 A | 7/1996 | Albright et al. | 514/220 |
| 5,612,334 A | 3/1997 | Alright et al. | 514/220 |
| 5,880,122 A | 3/1999 | Trybulski et al. | 514/220 |
| 6,194,407 B1 | 2/2001 | Failli et al. | 514/220 |
| 6,268,360 B1 | 7/2001 | Failli et al. | 514/220 |

FOREIGN PATENT DOCUMENTS

| | | |
|---|---|---|
| EP | 0127135 | 12/1984 |
| EP | 0306860 | 3/1989 |
| EP | 0472166 | 2/1992 |
| EP | 0636625 | 2/1995 |
| EP | 0990650 | 4/2000 |
| FR | 4999 M | 5/1967 |
| JP | 0881460 | 3/1996 |
| WO | WO 95/34540 | 12/1995 |
| WO | WO 96/22282 | 7/1996 |
| WO | WO 97/22591 | 6/1997 |
| WO | WO 99/06409 A1 | 2/1999 |
| WO | WO00/46228 | 8/2000 |
| WO | WO 01/22942 A1 | 4/2001 |
| WO | WO 01/22969 A2 | 4/2001 |
| WO | WO 01/49682 A1 | 7/2001 |
| WO | WO 02/00626 A1 | 1/2002 |

OTHER PUBLICATIONS

Derwent Abstract, 98-077100/07 (WO 97/49707).
Katritzky et al., "Efficient conversion of nitriles to amides with basic hydrogen peroxide in dimethyl sulfoxide," *Synthesis* (1989) pp. 949-950.
Hales et al. "Rearrangement reactions of bicyclic systems. Part V. 1 Acid-catalysed rearrangements of 1,4-dihydro-1,5,8-trimethoxy-1,4-ethenonaphthalene and the remarkable effect of aromatic methoxy-groups on the course of the reaction," *Tedtahedron* (1995) 51(27):7403-7410.
Cervoni, P. and Chan, P.S., Diuretic Agents, in Kirk-Othmer: Encyclopedia of Chemical Technology, 4th Ed., Wiley, vol. 8, 398-432, 1993.
Jackson, E.K., Goodman's and Gilman's The Pharmacological Basis of Therapeutics, 9th Ed., Eds, Hardman, Limbird, Molinoff, Ruddon and Gilman, McGraw-Hill, New York, pp. 715-731, 1996.
Alami et al., Tetrahedron Lett., 34, 6403, (1993).
Albini, A., Synthesis, 263 (1993).
Brenes-Pereira, C., Texas Heart Institute Journal, 24 (2), 118 (1997).
Burggraaf, J. et al., Clin. Sci. 86, 497 (1994).
Cabri et al., Tetrahedron Lett., 32, 1753 (1991).
Cash, J.D. et al., Brit. J. Haematol, 27, 363 (1974).
Cecchi, L. et al., J. Het. Chem., 20, 871 (1983).
Coffen et al., J. Org. Chem., 49, 296 (1984).

(Continued)

*Primary Examiner*—Brenda Coleman
(74) *Attorney, Agent, or Firm*—Cozen O'Connor

(57) ABSTRACT

Novel compounds of Formula (I)

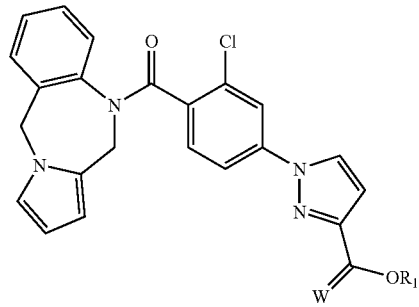

Formula (I)

and pharmaceutically acceptable salts thereof, and pharmaceutical formulations containing such compounds which are useful as anti-aquaretic agents in the treatment of nocturnal urinary enuresis, nocturnal urinary urgency, and/or similar conditions.

12 Claims, No Drawings

OTHER PUBLICATIONS

Coppola et al., J. Het. Chem., 11, 51 (1974).
Craig et al., Tetrahedron Lett., 4025 (1979).
David, J-L., Regulatory Peptides, 45, 311 (1993).
du Vigneaud, V. et al., J. Am. Chem. Soc., 76, 4751 (1954).
Farina et al., J. Org. Chem., 59, 5905 (1994).
Hallstrom, et al., Tetrahedron Lett., 667 (1980).
Huguenin et al., Helv. Chim. Acta, 49, 695 (1966).
Inanaga et al., Bull. Chem. Soc. Jpn., 52, 1989 (1979).
Jones, R.A., Aldrichimica ACTA, 9(3), 35 (1976).
Kantlehner et al., Chem. Ber., 105, 1340 (1972).
Khuthier, A-H. et al., J. Chem. Soc. Chem. Commun., 9 (1979).
Klaubert, D.H., J. Het. Chem., 22, 333 (1985).
Knorr et al., J. Org. Chem., 49, 1288 (1984).
Kosugi et al., Bull. Chem. Soc. Jpn., 60, 767 (1987).
Lethagen, S., Ann. Hematol., 69, 173 (1994).
Ligouri et al., Tetrahedron, 44, 1255 (1988).
Lin et al., J. Het. Chem., 14, 345 (1977).
Manning et al., J. Med. Chem., 35, 3895 (1992).
Manning et al., J. Med. Chem., 35, 382 (1992).
Martina et al., Synthesis, 8, 613 (1991).
Martinez et al., J. Med. Chem., 35, 620 (1992).
Mayet et al., J. of the Royal College of Physicians of London, 31 (3), 313 (1997).
Murray, R.W., Chem. Rev., 1187 (1989).
Oliver et al., J. Physiol. (London), 18, 277 (1895).
Reed et al., J. Org. Chem., 52, 3491 (1987).
Ruffolo et al., Drug News and Perspective, 4(4), 217 (May 1991).
Sonogashira et al., Tetrahedron Lett., 4467 (1975).
Street et al., J. Med. Chem., 36, 1529 (1993).
Williams, P.D., J. Med. Chem., 35, 3905 (1992).

BIOLOGICALLY ACTIVE VASOPRESSIN AGONIST METABOLITES

This application is a continuation-in-part of U.S. Ser. No. 09/122,020 filed Jul. 24, 1998 now U.S. Pat. No. 6,511,974, the entire disclosure of which is herein incorporated by reference.

FIELD OF THE INVENTION

The present invention concerns novel compounds having vasopressin agonist activity, as well as methods of treatment and pharmaceutical compositions utilizing the same.

BACKGROUND OF THE INVENTION

Vasopressin (antidiuretic hormone, ADH), a nine amino acid peptide hormone and neurotransmitter, is synthesized in the hypothalamus of the brain and is transported through the supraopticohypophyseal tract to the posterior pituitary where it is stored. Upon sensing an increase of plasma osmolality by brain osmoreceptors or a decrease of blood pressure or blood volume detected by the baroreceptors and volume receptors, vasopressin is released into the blood circulation where it activates vasopressin $V_{1a}$ receptors on blood vessels to cause vasoconstriction to raise blood pressure and vasopressin $V_2$ receptors of the nephrons of the kidney to retain mainly water, and to a lesser degree electrolytes, to expand the blood volume (Cervoni P. and Chan P. S., Diuretic Agents, In Kirk-Othmer: Encyclopedia of Chemical Technology, 4th Ed., Wiley, Volume 8, 398–432, 1993.). The existence of vasopressin in the pituitary was known as early as 1895 (Oliver, H. and Schaefer, *J. Physiol.* (London) 18: 277–279, 1895). The determination of the structure and the complete synthesis of vasopressin were accomplished by duVigneaud and co-workers in 1954 (duVigneaud, V., Gish, D. T., and Katsoyannis, *J. Am. Chem. Soc.* 76: 4751–4752, 1954.).

Vasopressin $V_{1a}$ receptors are mediated through the phosphatidylinositol pathway. Activation of vasopressin $V_{1a}$ receptors causes contraction of the smooth muscle of the blood vessels so as to raise blood pressure. The actions of the vasopressin $V_2$ receptors are mediated through activation of the adenylate cyclase system and elevation of intracellular levels of cAMP. The activation of the vasopressin $V_2$ receptors by vasopressin or vasopressin-like (peptide or nonpeptide) compounds increases water permeability of the collecting ducts of the nephron and permits the reabsorption of a large quantity of free water. The end result is the formation and excretion of a concentrated urine, with a decrease of urine volume and an increase of urinary osmolality.

Vasopressin plays a vital role in the conservation of water by concentrating the urine at the site of the collecting ducts of the kidney. The collecting ducts of the kidney are relatively impermeable to water without the presence of vasopressin at the receptors; and therefore, the hypotonic fluid formed after filtering through the glomeruli, passing the proximal convoluted tubules, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water, and hence water is reabsorbed and a concentrated urine is excreted. In patients and animals with central or neurogenic diabetes insipidus, the synthesis of vasopressin in the brain is defective; and therefore, they produce no or very little vasopressin, but their vasopressin receptors in the kidneys are normal. Because they cannot concentrate the urine, they may produce as high as 10 times the urine volume of their healthy counterparts, and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and help provide the ability of the recipient to temporarily delay urination, whenever desirable.

Vasopressin, through activation of its $V_{1a}$ receptors, exerts vasoconstricting effects so as to raise the blood pressure. A vasopressin $V_{1a}$ receptor antagonist will counteract this effect. Vasopressin and vasopressin agonists release factor VIII and von Willebrand factor so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, E. K., Vasopressin and other agents affecting the renal conservation of water. In: Goodman's and Gilman's The Pharmacological Basis of Therapeutics, 9th ed., Eds. Hardman, Limbird, Molinoff, Ruddon and Gilman, McGraw-Hill, New York, pp.715–731, 1996, Lethagen, S., *Ann. Hematol.*, 69; 173–180 (1994), Cash, J. D. et al., *Brit. J. Haematol.* 27; 363–364,1974., David, J-L., *Regulatory Peptides*, 45; 311–317, 1993, and Burggraaf, J., et al., *Clin. Sci.* 86; 497–503 (1994).

The following references describe peptide vasopressin antagonists: M. Manning et al., *J. Med. Chem.*, 35, 382 (1992); M. Manning et al., *J. Med. Chem.*, 35, 3895(1992); H. Gavras and B. Lammek, U.S. Pat. No. 5,070,187 (1991); M. Manning and W. H. Sawyer, U.S. Pat. No. 5,055,448 (1991) F. E. Ali, U.S. Pat. No. 4,766,108(1988); R. R. Ruffolo et al., *Drug News and Perspective*, 4(4), 217,(May 1991). P. D. Williams et al., have reported on potent hexapeptide oxytocin antagonists [*J. Med. Chem.*, 35, 3905 (1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed. Albright et al. describe tricyclic diazepines as vasopressin and oxytocin antagonists in U.S. Pat. No. 5,516, 774 (May 14,1996); tetrahydrobenzodiazepine derivatives as vasopressin antagonists are disclosed in JP 08081460-A (Mar. 26, 1996); Ogawa, et al. disclose benzoheterocyclic derivatives as vasopressin and oxytocin antagonists, and as vasopressin agonists in WO 9534540-A; Albright, et al. disclose tricyclic benzazepine derivatives as vasopressin antagonists in U.S. Pat. No. 5,512,563 (Apr. 30, 1996); and Venkatesan, et al. disclose tricyclic benzazepine derivatives as vasopressin and oxytocin antagonists in U.S. Pat. No. 5,521,173 (May 28,1996).

As mentioned above, desmopressin (1-desamino-8-D-arginine vasopressin) (Huguenin, Boissonnas, *Helv. Chim. Acta*, 49, 695 (1966)) is a vasopressin agonist. The compound is a synthetic peptide with variable bioavailability. An intranasal route is poorly tolerated and an oral formulation for nocturnal enuresis requires a 10–20 fold greater dose than by intranasal administration.

SUMMARY OF THE INVENTION

This invention provides novel compounds of Formula (I)

Formula (I)

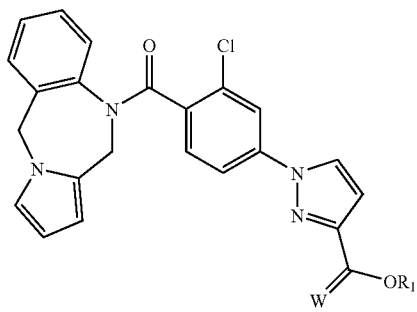

wherein
- W represents either a double-bonded O or two single-bonded H;
- $R_1$ is selected from the group consisting of R, $R_3$—X—$R_2$—, $R_3$—S(O)—, $R_3$—S(O)$_2$—, —SO$_3$R$_4$, —S(O)$_2$N(R)$_2$, and D-glucuronide, when W is hydrogen, or $R_1$ is selected from the group consisting of hydrogen, alkyl, cycloalkyl, aryl, arylalkyl, heteroaryl, and heteroarylalkyl, when W is oxygen;
- $R_2$ is selected from the group consisting of alkylene, cylcoalkylene, alkylene-X-alkylene, alkylene-X-cycloalkylene, cycloalkylene-X-alkylene, and cycloalkylene-X-cycloalkylene;
- $R_3$ is selected from the group consisting of alkyl, aryl, heteroaryl, cycloalkyl, alkenyl, cycloalkenyl, alkynyl, alkenyl-X-alkylene, cycloalkenyl-X-alkylene, and perfluoroalkyl;
- $R_4$ is selected from the group consisting of hydrogen and $R_3$;
- R is independently selected from the group consisting of hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxy-(C$_1$–C$_6$)alkyl, alkoxyalkyl, alkylthioalkyl, acyl, alkoxycarbonyl, —C(O)NH$_2$, alkylaminocarbonyl, dialkylaminocarbonyl, alkylaminoalkyl, and dialkylaminoalkyl, and when two R groups are bonded to the same atom the two R groups together may form an alkylene group;
- X is selected from the group consisting of oxygen, —NR—, —S(O)$_m$—, —C(O)—, —OC(O)—, —C(O)O—, —NRC(O)—, and —C(O)NR—; and
- m is an integer selected from 0, 1, and 2,
- and the racemates, enantiomers, and pharmaceutically acceptable salts thereof.

The present invention also provides a pharmaceutical composition which comprises a compound of this invention in a therapeutically or diagnostically effective amount in combination or association with a pharmaceutically acceptable carrier or excipient. The compositions are preferably adapted for oral administration, including sublingual administration. However, those skilled in the art will readily appreciate that they may be adapted for other modes of administration, including, but not limited to, parenteral, intrabronchial inhalation or insufflation, rectal, intravaginal, topical, intranasal, intraocular, or transdermal administration. To maintain consistency of administration, it is preferred that a composition of the invention is in the form of a unit dose.

Also according to the present invention there is provided a method of treating nocturnal urinary enuresis and/or noctural urinary urgency in humans or other mammals which comprises administering to a human or other mammal an anti-aquaretic effective amount of a compound of the present invention or a pharmaceutical composition thereof.

DETAILED DESCRIPTION

The present invention provides substituted novel 10,11-dihydro-5H-pyrrolo[2,1-c][1,4]benzodiazepine amides and related compounds represented by Formula (I) above. These compounds, compositions, and methods are useful in mammals, especially *homo sapiens*, as pharmacologically active agents with analytical, diagnostic, or therapeutic properties in physiological states where an anti-aquaretic component is operative, and where aqueous and electrolytic balance and control are required; such as, in nocturnal urinary enuresis and nocturnal urinary urgency. The compounds of the present invention may also be useful as pharmaceutical intermediates for the synthesis of novel useful compounds of the like described above.

A preferred group of compounds of the present invention are those of the formula Formula (II)

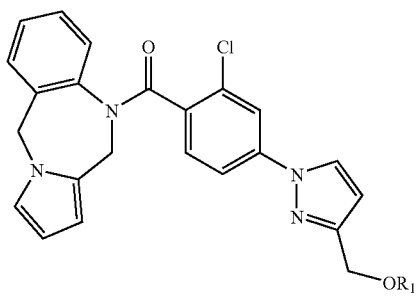

where $R_1$ is as defined above. A preferred subset of the compounds of Formula (II) are those in which $R_1$ is selected from the group consisting of hydrogen, alkyl, alkenyl, cycloalkyl, cycloalkenyl, aryl, arylalkyl, $R_3$—S(O)—, $R_3$—S(O)$_2$—, —SO$_3$R$_4$, —S(O)$_2$N(R)$_2$, hydroxy-(C$_1$–C$_6$)alkyl, alkoxyalkyl, alkylthioalkyl, acyl, alkoxycarbonyl, —C(O)NH$_2$, alkylaminocarbonyl, dialkylaminocarbonyl, alkylaminoalkyl, and dialkylaminoalkyl, where R, $R_3$, and $R_4$ are as defined above.

The term "alkyl", employed alone, is defined herein as, unless otherwise stated, either a (C$_1$–C$_{20}$) straight chain or (C$_3$–C$_{20}$) branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like. It is preferred that straight chain alkyl moieties have 1–6 carbon atoms, and branched alkyl moieties have 3–8 carbon atoms.

The term "alkenyl", employed alone, is defined herein as, unless otherwise stated, either a (C$_2$–C$_{20}$) straight chain or (C$_3$–C$_{20}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like. It is preferred that straight chain alkenyl moieties have 2–7 carbon atoms, and branched alkenyl moieties have 3–8 carbon atoms.

The term "alkynyl", employed alone, is defined herein as, unless otherwise stated, either a ($C_2$–$C_{20}$) straight chain or ($C_3$–$C_{20}$) branched-chain monovalent hydrocarbon moiety containing at least one triple bond. Examples of alkynyl moieties include, but are not limited to, chemical groups such as ethynyl, 1-propynyl, 1-(2-propynyl), 3-butynyl, and higher homologs, isomers, and the like. It is preferred that straight chain alkynyl moieties have 2–7 carbon atoms, and branched alkynyl moieties have 3–8 carbon atoms.

The term "alkylene", employed alone or in combination with other terms, is defined herein as, unless otherwise stated, either a ($C_1$–$C_{20}$) straight chain or ($C_2$–$C_{20}$) branched-chain bivalent hydrocarbon moiety derived from an alkane; or a ($C_2$–$C_{20}$) straight chain or branched-chain bivalent hydrocarbon moiety derived from an alkene. Such hydrocarbon alkylene moieties may be fully saturated, or mono or polyunsaturated, and may exist in the E or Z configurations. The compounds of this invention are meant to include all possible E and Z configurations. Examples of saturated and unsaturated hydrocarbon alkylene moieties include, but are not limited to, bivalent chemical groups such as —$CH_2$—, —$CH_2CH_2$—, —$CH_2CH_2CH_2$—, —$CH_2CH_2CH_2CH_2$—, —CH=CH—, —CH=CHCH=CH—, vinylidene, and higher homologs, isomers, and the like. Preferred alkylene chains have 2–7 carbon atoms.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3–10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3–10 carbon atoms containing at least one double bond, wherein the carbon atoms are located inside or outside of the ring system. Any suitable ring position of the cycloalkenyl moiety may be covalently linked to the defined chemical structure. Examples of cycloalkenyl moieties include, but are not limited to, chemical groups such as cyclopropenyl, cyclopropenylmethyl, cyclobutenyl, cyclopentenyl, cyclohexenyl, cyclohexenylmethyl, cyclohexenylethyl, cycloheptenyl, norbornenyl, and homologs, isomers, and the like.

The term "cycloalkylene", employed alone, is defined herein as, unless otherwise stated, a bivalent moiety of 3–10 carbon atoms derived from a monocyclic, bicyclic, tricyclic, fused, bridged, or spiro hydrocarbon. Such hydrocarbon cycloalkylene moieties may be fully saturated, or mono or polyunsaturated, and may exist in the E or Z configurations. The compounds of this invention are meant to include all possible E and Z configurations. Any suitable ring position of the cycloalkylene moiety may be covalently linked to the defined chemical structure. Examples of saturated and unsaturated hydrocarbon cycloalkylene moieties include, but are not limited to, bivalent chemical groups such as cyclopropylene, cyclopentylene, cyclohexylene, cyclohexenylene, trans-decahydronaphthalenylene, spiro[3.3]heptenylene, and higher homologs, isomers, and the like.

The terms "halo" or "halogen", employed alone or in combination with other terms, is defined herein as, unless otherwise stated, a fluorine, chlorine, bromine, or iodine atom.

The term "monofluoroalkyl", employed alone, is defined herein as, unless otherwise stated, either a ($C_1$–$C_{10}$) straight chain or ($C_3$–$C_{10}$) branched-chain monovalent saturated hydrocarbon moiety containing only one fluorine atom. Examples of monofluoroalkyl moieties include, but are not limited to, chemical groups such as —$CH_2F$, —$CH_2CH_2F$, —$CH(CH_3)CH_2CH_2F$, and higher homologs, isomers, and the like. Preferred chain lengths are from 1–6 carbon atoms for straight chains and from 3–8 carbon atoms for branched chains.

The term "monofluoroalkenyl", employed alone, is defined herein as, unless otherwise stated, either a ($C_2$–$C_{10}$) straight chain or ($C_3$–$C_{10}$) branched-chain monovalent unsaturated hydrocarbon moiety, containing only one fluorine atom and at least one double bond. Examples of monofluoroalkenyl moieties include, but are not limited to, chemical groups such as —CH=$CH_2F$, —$CH_2$CH=$CH_2F$, —CH=$CHCH_2F$, —C($CH_3$)=CHF and higher homologs, isomers, and the like. Preferred chain lengths are from 2–7 carbon atoms for straight chains and from 3–8 carbon atoms for branched chains.

The term "perfluoroalkyl", employed alone or in combination with other terms, is defined herein as, unless otherwise stated, either a ($C_1$–$C_{10}$) straight chain or ($C_3$–$C_{10}$) branched-chain monovalent saturated hydrocarbon moiety containing two or more fluorine atoms. Examples of perfluoroalkyl moieties include, but are not limited to, chemical groups such as trifluoromethyl, —$CH_2CF_3$, —$CF_2CF_3$, and —CH($CF_3$)$_2$, and homologs, isomers, and the like. Preferred chain lengths are from 1–7 carbon atoms for straight chains and from 3–8 carbon atoms for branched chains.

The term "aryl", employed alone or in combination with other terms, is defined herein as, unless otherwise stated, an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. It is preferred that the aryl moiety contain 6–14 carbon atoms.

The term "arylalkyl", employed alone or in combination with other terms, is defined herein as, unless otherwise stated, an aryl group, as herein before defined, suitably substituted on any open ring position with an alkyl moiety wherein the alkyl chain is either a ($C_1$–$C_6$) straight or ($C_2$–$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heteroaryl", employed alone or in combination with other terms, is defined herein as, unless otherwise stated, an aromatic heterocyclic ring system, which may be a single ring (monocyclic) or multiple rings (bicyclic, up to three rings) fused together or linked covalently. The rings may contain from one to four hetero atoms selected from nitrogen (N), oxygen (O), or sulfur (S), wherein the nitrogen or sulfur atom(s) are optionally oxidized, or the nitrogen atom(s) are optionally substituted or quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

The term "heteroarylalkyl", employed alone or in combination with other terms, is defined herein as, unless otherwise stated, a heteroaryl group, as herein before defined, suitably substituted on any open ring position with an alkyl moiety, wherein the alkyl chain is either a ($C_1$–$C_6$) straight or ($C_2$–$C_7$) branched-chain saturated hydrocarbon moiety. Examples of heteroarylalkyl moieties include, but are not limited to, chemical groups such as furanylmethyl, thienylethyl, indolylmethyl, and the like.

Heteroaryl chemical groups, as herein before defined, also include saturated or partial saturated heterocyclic rings. Examples of saturated or partially saturated heteroaryl moieties include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "acyl", employed alone or in combination with other terms, is defined herein as, unless otherwise stated, an alkyl, arylalkyl, or heteroarylalkyl, ($C_2$–$C_{10}$) straight chain, or ($C_4$–$C_{11}$) branched-chain monovalent hydrocarbon moiety; wherein the carbon atom, covalently linked to the defined chemical structure, is oxidized to the carbonyl oxidation state. Such hydrocarbon moieties may be mono or polyunsaturated, and may exist in the E or Z configurations. The compounds of this invention are meant to include all possible E and Z configurations. Examples of acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "hydroxyalkyl", employed alone or in combination with other terms, is defined herein as, unless other-wise stated, a ($C_1$–$C_{10}$) straight chain hydrocarbon, terminally substituted with a hydroxyl group. Examples of hydroxyalkyl moieties include chemical groups such as —$CH_2OH$, —$CH_2CH_2OH$, —$CH_2CH_2CH_2OH$, and higher homologs.

The term "alkoxy", employed alone or in combination with other terms, is defined herein as, unless otherwise stated, either a ($C_1$–$C_{10}$) straight chain or ($C_3$–$C_{10}$) branched-chain hydrocarbon covalently bonded to an oxygen atom. Examples of alkoxy moieties include, but are not limited to, chemical groups such as methoxy, ethoxy, isopropoxy, sec-butoxy, tert-butoxy, decanoxy, and homologs, isomers, and the like.

The terms "aryloxy" or "heteroaryloxy", employed alone or in combination with other terms, or unless otherwise stated, are aryl or heteroaryl groups, as herein before defined, which are further covalently bonded to an oxygen atom. Examples of aryloxy or heteroaryloxy moieties include, but are not limited to, chemical groups such as $C_6H_5O$—, 4-pyridyl-O—, and homologs, isomers, and the like.

The term "carbonyl", employed alone or in combination with other terms, is defined herein as, unless otherwise stated, a bivalent one-carbon moiety further bonded to an oxygen atom with a double bond. An example is

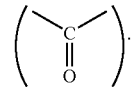

The term "alkoxycarbonyl", employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

The term "alkylthio", employed alone or in combination with other terms, is defined herein as, unless otherwise stated, either a ($C_1$–$C_{10}$) straight chain or ($C_3$–$C_{10}$) branched-chain hydrocarbon moiety covalently bonded to a sulfur atom. Examples of alkylthio moieties include, but are not limited to, chemical groups such as methylthio, ethylthio, isopropylthio, sec-butylthio, tert-butylthio, decanylthio, and homologs, isomers, and the like. It is preferred that straight chain alkylthio moieties have 1–6 carbon atoms, and branched alkylthio moieties have 3–8 carbon atoms.

The terms "arylthio" or "heteroarylthio", employed alone or in combination with other terms, or unless otherwise stated, are aryl or heteroaryl groups, as herein before defined, which are further covalently bonded to a sulfur atom. Examples of arylthio or heteroarylthio moieties include, but are not limited to, chemical groups such as $C_6H_5S$—, 4-pyridyl-S—, and homologs, isomers, and the like.

The terms "alkoxyalkyl", or "alkylthioalkyl", employed alone or in combination with other terms, are, unless otherwise stated, an alkoxy or alkylthio group, as herein before defined, which is further covalently bonded to an unsubstituted ($C_1$–$C_{10}$) straight chain or unsubstituted ($C_2$–$C_{10}$) branched-chain hydrocarbon. Examples of alkoxyalkyl or alkylthioalkyl moieties include, but are not limited to, chemical groups such as, methoxymethyl, methylthioethyl, ethylthioethyl, isopropylthiomethyl, sec-butylthioethyl, —CH₂CH(CH₃)OCH₂CH₃, and homologs, isomers, and the like. It is preferred that straight chain alkoxyalkyl or alkylthioalkyl moieties have 1–6 carbon atoms, and branched alkoxyalkyl or alkylthioalkyl moieties have 3–8 carbon atoms.

The terms "aryloxyalkyl", "heteroaryloxyalkyl", "arylthioalkyl", or "heteroarylthioalkyl", employed alone or in combination with other terms, or unless otherwise stated, are aryloxy, heteroaryloxy, arylthio, or heteroarylthio groups, as herein before defined, which are further covalently bonded to an unsubstituted ($C_1$–$C_{10}$) straight chain or unsubstituted ($C_2$–$C_{10}$) branched-chain hydrocarbon. Examples of aryloxyalkyl, heteroaryloxyalkyl, arylthioalkyl, and heteroarylthioalkyl moieties include, but are not limited to, chemical groups such as $C_6H_5OCH_2$—, $C_6H_5OCH(CH_3)$—, 4-pyridyl-O—CH₂CH₂—, $C_6H_5SCH_2$—, $C_6H_5SCH(CH_3)$—, 4-pyridyl-S—CH₂CH₂—, and homologs, isomers, and the like. It is preferred that straight chain aryloxyalkyl, heteroaryloxyalkyl, arylthioalkyl, or heteroarylthioalkyl moieties have 1–6 carbon atoms, and branched aryloxyalkyl, heteroaryloxyalkyl, arylthioalkyl, or heteroarylthioalkyl moieties have 3–8 carbon atoms.

The term "alkylamino", employed alone or in combination with other terms, or unless otherwise stated, is a moiety with one alkyl group, wherein the alkyl group is an unsubstitued ($C_1$–$C_6$) straight chain hereunto before defined alkyl group or an unsubstitued ($C_3$–$C_8$) hereunto before defined cycloalkyl group. Examples of alkylamino moieties include, but are not limited to, chemical groups such as —NH(CH₃), —NH(CH₂CH₃), —NH-cyclopentyl, and homologs, and the like.

The term "dialkylamino", employed alone or in combination with other terms, or unless otherwise stated, is a moiety with two independent alkyl groups, wherein the alkyl groups are unsubstitued ($C_1$–$C_6$) straight chain hereunto before defined alkyl groups or unsubstitued ($C_3$–$C_8$) hereunto before defined cycloalkyl groups. The two groups may be linked to form an unsubstituted ($C_1$–$C_6$)-alkylene- group. Examples of dialkylamino moieties include, but are not limited to, chemical groups such as —N(CH₃)₂, —N(CH₂CH₃)₂, —NCH₃(CH₂CH₃),

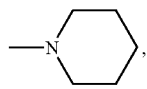

and homologs, and the like.

The term "alkylaminoalkyl" employed alone or in combination with other terms, or unless otherwise stated, is an alkylamino moiety, as herein before defined, which is further covalently bonded to a straight chain alkyl group of 1–6 carbon atoms. Examples of alkylaminoalkyl moieties include, but are not limited to, chemical groups such as —CH₂NH(CH₃), —CH₂CH₂NH(CH₂CH₃), —CH₂CH₂CH₂NH(CH₂CH₃), and homologs, and the like.

The term "dialkylaminoalkyl" employed alone or in combination with other terms, or unless otherwise stated, is a dialkylamino moiety, as herein before defined, which is further covalently bonded to a straight chain alkyl group of 1–6 carbon atoms. Examples of dialkylaminoalkyl moieties include, but are not limited to, chemical groups such as —CH₂N(CH₃)₂, —CH₂CH₂N(CH₂CH₃)₂, CH₂CH₂CH₂NCH₃(CH₂CH₃), and homologs, and the like.

The terms "alkylaminocarbonyl" or "dialkylaminocarbonyl", employed alone, or unless otherwise stated, are alkylamino or dialkylamino moieties, as herein before defined, which are further bonded to a carbonyl group. Examples of alkylaminocarbonyl or dialkylaminocarbonyl moieties include, but are not limited to, chemical groups such as —C(O)NH(CH₃), —C(O)N(CH₂CH₃)₂, —C(O)NCH₃(CH₂CH₃), and homologs, and the like.

Each of the above terms (e.g., alkyl, aryl, heteroaryl) includes unsubstituted, monosubstituted, and polysubstituted forms of the indicated radical or moiety. Substituents for each type of moiety are provided below.

Substituents for alkyl, alkenyl, alkynyl, cycloalkyl, cycloalkenyl, alkylene, cycloalkylene, the alkyl portion of arylalkyl and heteroarylalkyl, saturated or partially saturated heterocyclic rings, and acyl or carbonyl moieties are, employed alone or in combination with other terms, selected from the group consisting of —R', OR', =O, =NR', =N—OR', —NR'R", —SR', halo, trifluoromethyl, trifluoromethoxy, —OC(O)R', CO₂R', —C(O)NR'R", —OC(O)NR'R", —NR"C(O)R', —NR"CO₂R', —NR'C(O)NR'R", —NH—C(NH₂)=NH, —NR'C(NH₂)=NH, —NH—C(NH₂)=NR', —S(O)R', —S(O)₂R', —S(O)₂NR'R", cyano, and nitro; wherein, R' or R" are each, independently, hydrogen, unsubstituted ($C_1$–$C_6$)alkyl, unsubstituted ($C_3$–$C_7$)cycloalkyl, aryl, aryl-($C_1$–$C_3$)alkyl, aryloxy-($C_1$–$C_3$) alkyl, arylthio-($C_1$–$C_3$)alkyl, heteroaryl, heteroaryl-($C_1$–$C_3$)alkyl, heteroaryloxy-($C_1$–$C_3$) alkyl, or heteroarylthio-($C_1$–$C_3$) alkyl groups; or, if optionally taken together, may be linked as an -alkylene- group to form a ring.

The aryl or heteroaryl moieties, employed alone or in combination with other terms, may be optionally mono-, di- or tri-substituted with substituents selected from the group consisting of —R', —OR', —SR', —C(O)R', —CO₂R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)₂R', —SO₃R', —S(O)₂NR'R", —CO₂R', —C(O)NR'R", —OC(O)NR'R", —NR"C(O)R', —NR"CO₂R', —NR'C(O)NR'R", —NH—C(NH₂)=NH, —NR'C(NH₂)=NH, —NH—C(NH₂)=NR', —S(O)R', and —S(O)₂R'; wherein, R' or R" are each, independently, hydrogen, ($C_1$–$C_6$)alkyl, ($C_3$–$C_7$)cycloalkyl, aryl, aryl-($C_1$–$C_3$) alkyl, aryloxy-($C_1$–$C_3$)alkyl, arylthio-($C_1$–$C_3$)alkyl, heteroaryl, heteroaryl-($C_1$–$C_3$) alkyl, heteroaryloxy-($C_1$–$C_3$)alkyl, or heteroarylthio-($C_1$–$C_3$)alkyl groups; or, if optionally taken together, may be linked as an -alkylene- group to form a ring.

A pro-drug is defined as a compound which is convertible by in vivo enzymatic or non-enzymatic metabolism (e.g. hydrolysis) to a compound of Formula (I) or Formula (II); wherein, $R_1$ is a hydrogen atom.

The compounds of the present invention may contain an asymmetric atom, and some of the compounds may contain one or more asymmetric atoms or centers, which may thus give rise to optical isomers (enantiomers) and diastereomers. While shown without respect to the stereochemistry in Formula (I) or Formula (II), the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers may be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which may be obtained in pure form by standard separation procedures known to those skilled in the art, and include, but are not limited to, column chromatography, thin-layer chromatography, and high-performance liquid chromatography.

The compounds of the present invention may contain isotopes of atoms for diagnostic, therapeutic, or metabolic purposes. Such isotopes may or may not be radioactive.

Pharmaceutically acceptable salts of the compounds of Formula (I) or Formula (II) containing an acidic moiety can be formed from organic and inorganic bases. Suitable inorganic basic salts such as alkali metal salts include, but are not limited to, sodium, lithium, or potassium salts; other inorganic basic salts such as alkaline earth metal salts include, but are not limited to, calcium or magnesium salts. Suitable organic basic salts with ammonia or an organic amine include, but are not limited to, morpholine, thiomorpholine, piperidine, pyrrolidine, mono, di, or tri-lower alkylamine, for example ethyl tert-butyl-, diethyl-, diisopropyl-, triethyl-, tributyl- or dimethylprnpylamine, or mono, di, or trihydroxy lower alkylamine, for example mono, di, or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

Pharmaceutical Formulations and Preparations

It is understood that the effective dosage of the active compounds of this invention may vary depending upon the particular compound utilized, the mode of administration, the condition, and severity thereof, of the condition being treated, as well as the various physical factors related to the individual being treated. For use as anti-aquaretic agents in treating nocturnal urinary enuresis and nocturnal urinary urgency, generally satisfactory results may be obtained when the compounds of this invention are administered to the individual in need at a daily dosage of from about 0.01 mg to about 30 mg per kilogram of body weight, preferably administered in divided doses two to six times per day, or in a sustained release form. For most large mammals, the total daily dosage is from about 1 mg to about 2100 mg, preferably from about 1 to about 10 mg. In the case of a 70 kg human adult, the total daily dose will generally be from about 1 mg to about 10 mg and may be adjusted to provide the optimal therapeutic result.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, sweetening agents, lubricants, solubilizers, suspending agents, fillers, glidants, compression aids, binders, or tablet-disintegrating agents; it can also be an encapsulating material. In powders, the carrier is a finely divided solid which is in admixture with the finely divided active ingredient.

Solid dosage unit forms or compositions such as tablets, troches, pills, capsules, powders, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers are used in preparing liquid dosage forms such as solutions, suspensions, dispersions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution); alcohols, including monohydric alcohols such as ethanol and polyhydric alcohols such as glycols and their derivatives; lethicins, and oils such as fractionated coconut oil and arachis oil. For parenteral administration, the liquid carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

A liquid pharmaceutical composition such as a syrup or elixir may contain, in addition to one or more liquid carriers and the active ingredients, a sweetening agent such as sucrose, preservatives such as methyl and propyl parabens, a pharmaceutically acceptable dye or coloring agent, or a flavoring agent such as cherry or orange flavoring.

Liquid pharmaceutical compositions which are sterile solutions or suspensions can be administered intraocularly or parenterally, for example, by intramuscular, intraperitoneal or subcutaneous injection. Sterile solutions can also be administered intravenously. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing a liquid carrier, for example, water, ethanol, polyol (e.g. glycerol, propylene glycol and liquid polyethylene glycol), suitable mixtures thereof, and vegetable oils. The liquid carrier may be suitably mixed with a surfactant such as hydroxypropylcellulose.

The compounds of the present invention may also be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may be administered topically, or also transdermally through the use of a transdermal patch containing the active compound and a carrier that is inert to the active compound, which is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The compounds of the present invention can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. Although not limited to any one or several sources, classic texts such as Smith, M. B.; March, J. *March's Advanced Organic Chemistry: Reactions, Mechanisms, and Structure,* 5$^{th}$ ed.; John Wiley & Sons: New York, 2001; and Greene, T. W.; Wuts, P. G. M. *Protective Groups in Organic Synthesis,* 3rd ed.; John Wiley & Sons: New York, 1999 are useful and recognized reference textbooks of organic synthesis known to those in the art. The following synthetic schemes are designed to illustrate, but not limit, general procedures for the preparation of compounds of the type illustrated. An exemplary general procedure for the convenient preparation of such pyrazole pyrrolobenzodiazepines is shown in the following schemes:

Scheme I

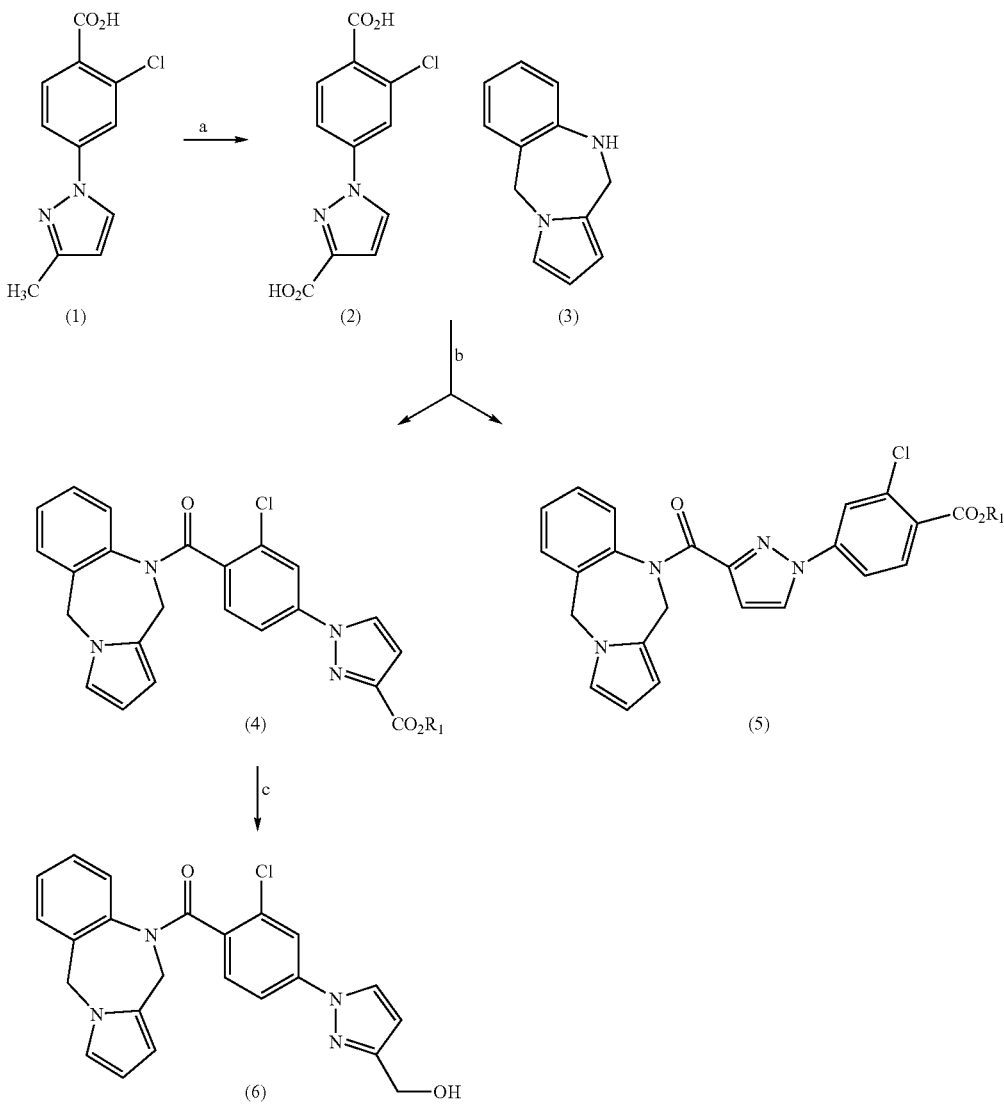

a. KMnO$_4$ (5.25 equiv.), 1N KOH, H$_2$O, 60–65° C., 4h., 2N HCl;
b. (COCl)$_2$, DMF (cat.), CH$_2$Cl$_2$, 0.5h., ROH; c. (4) Compound A, 2.0M LiBH$_4$ (20 equiv.), THF, 1.5h.

In scheme I, step a, the previously described intermediate (1) is reacted with an oxidizing agent such as potassium permanganate under alkaline conditions at a temperature of between 60–65° C. in an aqueous solvent mixture to obtain the diacid (2). In step b, treatment of (2) with oxalyl chloride, thionyl chloride or other commercially available or suitably known chlorinating agent produces the unisolated diacid chloride, which upon further treatment with the previously described (3) in a suitable solvent such as chloroform, 1,2-dichloroethane, or dichloromethane, and the like, affords, after quenching with an alcohol, a mixture of products. Chromatographic separation of the product compounds affords ester (4). In step c, treatment of ester (4) with an excess of a borohydride reducing agent such as lithium borohydride in a suitable solvent such as tetradyrofuran affords the corresponding methanol (6).

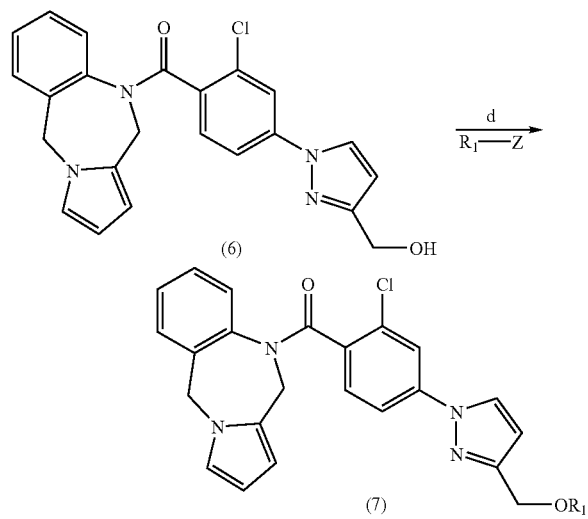

d. R$_1$-Z, base, solvent

A pro-drug is a compound of Formula (I) or (II) that could facilitate absorption, inhibit or facilitate metabolism, affect distribution, or alter excretion of the pharmaceutically active agent. A pro-drug may be converted to the active pharmaceutical species by hydrolytic, enzymatic, or metabolic transformations. In scheme II, the desired alcohol (6) may be protected by alkylation or acylation of alcohol (6) to prepare (7). This could be for the purpose of further synthetic elaboration, or for the reason of preparing pro-drugs, metabolites, or conjugates of (6). Consequently, R$_1$-Z; wherein, R$_1$ is as herein before defined, and Z is a leaving group, such as, but not limited to, a chlorine, bromine, or iodine atom, or a triflate (—OSO$_2$CF$_3$) or anhydride moiety, or a hydroxy (such as in Mitsunobu chemistry) moiety, is reacted under alkylating or acylating conditions with (6), optionally in the presence of a base, such as, but not limited to, triethylamine, diisopropylethylamine, pyridine, triphenylphosphine, or potassium carbonate, and the like, and further optionally in the presence of a known promoter or catalyst, such as 4-(N,N-dimethylamino)pyridine at –78° C. to 80° C. for several hours to afford the protected alcohol (7).

Biological Data

In Vivo Methods

Method of Study Performance:

Rats:

All animals for this study were six to seven week old male rats obtained from Charles River Laboratories (Crl: CD (SD) IGS BR) and weighing between 180–250 grams after sixteen to eighteen hours of fasting. On arrival, all rats were assessed as to their general health by a member of the veterinary staff or other authorized personnel. A minimum period of three days for acclimation and quarantine was allowed between animal receipt and the start of dosing. During this time the animals were acclimatized and observed for the development of any infectious disease. Any animals considered unacceptable for use in this study were replaced with animals of similar age and weight from the same vendor. All animals were group-housed in compliance with the National Research Council's "Guide for the Care and Use of Laboratory Animals" at a registered and fully AAALAC accredited facility under a controlled temperature of between 18–26° C., a controlled relative humidity of between 30 to 70%, and 12 hour cycles of artificial lightness and darkness. All animals had access to Certified Rodent Diet (TEKLAD) or equivalent *ad libitum*, unless otherwise specified. Water was provided to the animals *ad libitum*, unless otherwise specified. Tests performed demonstrated no known contaminants in the diet or water which, at the levels detected, would be expected to interfere with the purpose, conduct, or outcome of the study. For purposes of animal welfare, the study protocol was reviewed by the Institutional Animal Care and Use Committee and complies with acceptable standard animal welfare and humane care. All rats were color coded with markings prior to dosing.

Vehicle Formulation:

The vehicle used in the study was 20% dimethyl sulfoxide (DMSO) in 0.25% methylcellulose. Vehicle preparation consisted of preparing a clear solution of 1 mL DMSO and 4 mL of a 0.25% solution of methylcellulose in distilled water. Following preparation, the vehicle was refrigerated until needed and allowed to equilibrate to room temperature prior to dose preparation and dosing.

Study Compound Formulation:

The test compounds were prepared by solubilizing the test compound in 1.0 mL of DMSO and adding 4.0 mL of a 0.25% solution of methylcellulose in distilled water, in accordance with the study protocols, and stored at room temperature prior to animal dosing.

Study Protocol:

The in vivo study protocols were performed in accordance with the method of R. M. Taylor and J. G. Topliss, *J. Med. Pharm. Chem.* (4) 312, 1962. All rats were fasted for approximately sixteen to eighteen hours before the initiation of the study. During this time, they were allowed water *ad libitum* up to one hour prior to initiation of the study. At study time, the rats were weighed, placed into groups of two animals per test compound and dose level and two vehicle controls, and administered the test compounds according to the treatment regimen. All animals were dosed at 10 mg/kg with a formulation concentration of 2.0 mg/mL of test compound. Immediately following oral dose administration, the rats were orally hydrated with distilled water (Roaring Springs Water Company, Lot number: 01120109371, Exp. 12 Jan. 2003) at 25 mL/kg. The rats were force-urinated by massage and placed in individual metabolism cages. Urine was collected over a four-hour period (±5 minutes). After four hours L±5 minutes), urine volumes were recorded, and the pH values of the urine determined. Urine electrolyte concentrations for sodium, potassium, and chloride ions were determined on a Hitachi Model 704 Automated Chemistry Analyzer. Urine Osmolality was determined using an Advanced Instruments Osmometer.

Following data collection, the animals were euthanized by carbon dioxide asphyxiation without exsanguination.

Method of Statistical Analysis:

The electrolyte concentrations for sodium, potassium, and chloride ions were expressed in terms of μEq of electrolyte excreted per 100 grams of animal weight. Diuretic effects of the test compounds on urinary volume output, pH, electrolytes, and osmolality were expressed in mean tabular form. Statistically significant effects were determined by ANOVA with a relevant Multiple Comparison Test.

In Vivo Results

Tables 1 and 2 provide data on the activity of a compound of the invention and a comparison against vehicle (negative control), and another active compound (positive control).

TABLE 1

Effects of reference and tested compounds on urine output and pH in normal conscious water-loaded rats orally dosed at 10 mg/kg.

| | Dose (mg/kg) | Urine Volume (mL) | % Change % Inc. or Dec. | pH |
|---|---|---|---|---|
| Ref. A* (−Control) | 0 | 5.5 | 0% | 6.77 |
| Ref. B** (+Control) | 10 | 1.0 | 82% Decrease | 6.50 |
| Example 1 Compound*** | 10 | 1.0 | 82% Decrease | 6.42 |

*No active compound (Vehicle)
**[2-Chloro-4-(3-methyl-pyrazol-1-yl)-phenyl]-(5H,11H)-pyrrolo[2,1-c][1,4]benzodiazepin-10-yl)-methanone
***(1-[3-Chloro-4-(5H-pyrrolo[2,1-c][1,4]benzodiazepin-10(11H)-ylcarbonyl)-phenyl]-1H-pyrazol-3-yl)methanol

TABLE 2

Effects of reference and tested compounds on urine Electrolyte Balance and Osmolality in normal conscious water-loaded rats orally dosed at 10 mg/kg.

| | Electrolyte Concentration | | | Electrolyte Excreted per 100 g Body Wt. | | | mEq Excreted per 4 hours | | | Osmolality mOsm/kg |
|---|---|---|---|---|---|---|---|---|---|---|
| | mEq/L $Na^+$ | mEq/L $K^+$ | mEq/L $Cl^-$ | μEq $Na^+$ | μEq $K^+$ | μEq $Cl^-$ | mEq $Na^+$ | mEq $K^+$ | mEq $Cl^-$ | |
| Ref. A | 10.0 | 7.5 | 10.0 | 25.5 | 19,0 | 25.5 | 0.055 | 0.041 | 0.055 | 198.0 |
| Ref. B | 25.5 | 75.8 | 62.0 | 12.0 | 35.7 | 29.5 | 0.026 | 0.076 | 0.062 | 1564.5 |
| Example 1 compound | 35.0 | 67.5 | 52.5 | 16.0 | 30.4 | 23.5 | 0.035 | 0.068 | 0.053 | 832.5 |

The following examples are presented to illustrate rather than limit the scope of this invention. Compounds described as homogeneous were determined to be 98% or greater a single peak (exclusive of enantiomers) by analytical reverse phase chromatographic analysis with 254 nM UV detection. Melting points are reported as uncorrected in degrees centigrade. The infrared data is reported as wavenumbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet, quintet; or br, broadened. Italicized elements or groups are those responsible for the chemical shifts. $^{13}C$ NMR chemical shift assignments were made by reasonable assignment from 2-D experiments. The yields given below are for informational purposes and may vary according to experimental conditions or individual techniques.

EXAMPLE 1

Step a 1-(4–Carboxy-3-chlorophenyl)-1H-pyrazole-3-carboxylic acid

A vigorously stirred solution of 2-chloro-4-(3-methyl-1 H-pyrazol-1-yl)benzoic acid (7.08 g, 30.0 mmol) and 1 N potassium hydroxide (30 mL, 30.0 mmol) in water (200 mL) was heated to between 60–65° C. and treated gradually over ninety minutes with several aliquots of solid potassium permanganate (Total: 49.78 g, 315 mmol, 5.25 equivalents). The mixture was heated for an additional 2.5 hours (4 hours total). After cooling to room temperature, the mixture was filtered and evaporated to a residue. The residue was dissolved in 2 N hydrochloric acid and extracted with ethyl acetate (3×). The combined organic phase was washed with water, dried over anhydrous sodium sulfate, filtered, and the solvent removed in vacuo to yield, after crystallization from a mixture of ethyl acetate-diethyl ether-hexane, the title compound (1.27 g, 4.8 mmol, 16%) as a homogeneous solid, m.p. 260–263° C.;

MS [(+APCI), m/z]: 267/269 $[M+H]^+$, contains one chlorine atom;

IR (Solid), $v_{max}$: 3000, 1695, 1600, 1280, 775 $cm^{-1}$;

$^1H$ NMR (400 MHz, DMSO-$d_6$) δ: 13.31–13.29 (br s, 2H, —$CO_2H$), 8.75 (d, J=2.6 Hz,1H, ArH-5-pyrazole), 8.10 (dd, J=1.3, 0.7 Hz,1H, ArH'-2'), 7.98 (s, 2H, ArH'-5',6'), 6.99 (d, J=2.6 Hz, 1H, ArH-4-pyrazole);

$^{13}C$ NMR (100 MHz, DMSO-$d_6$) δ: 165.8 (s, 1C, C=O), 162.6 (s, 1C, C=O), 146.2 (s, 1C), 141.5 (s, 1C), 133.4 (s, 1C), 132.7 (s, 1C), 130.4 (s, 1C), 129.0 (s, 1C), 120.4 (s, 1C), 117.3 (s, 1C), 110.8 (s, 1C).

Step b

Methyl 1-[3-chloro4-(5H-pyrrolo[2,1-c][1,4]benzodiazepin-10(11H)-ylcarbonyl)phenyl]-1H-pyrazole-3-carboxylate and

Methyl 2-chloro-4-[3-(5H-pyrrolo[2,1-c][1,4]benzodiazepin-10(11H)-ylcarbonyl)-1H-pyrazol-1-yl]benzoate A stirred suspension of 1-(4-carboxy-3-chlorophenyl)-1H-pyrazole-3-carboxylic acid (0.81 g, 3.0 mmol) and dimethyl formamide (0.02 g, 0.30 mmol) in dichloromethane (10 mL) was treated drop-wise under nitrogen at room temperature with a solution of oxalyl chloride (0.76 g, 6.0 mmol) in dichloromethane (10 mL). After stirring at room temperature for 0.25 hours, the resulting diacid chloride was treated rapidly with a solution of 10, 11-dihydro-5H-pyrrolo[2,1-c][1,4]benzodiazepine (0.55 g, 3.0 mmol) and N,N-diisopropylethylamine (0.78 g, 6.0 mmol) in dichloromethane. After stirring at room temperature for 0.5 hours, the reaction was quenched with dry methanol (3.0 mL) and evaporated in vacuo to a residue. The residue was dissolved in ethyl acetate and washed sequentially with 1 N hydrochloric acid and water. After drying over anhydrous sodium sulfate, the organic phase was filtered through a short column of silica gel to afford two fractions: Fraction A (0.54 g) and Fraction B (0.72 g). Fractions A and B were purified by preparative normal phase high-performance liquid chromatography on a Primesphere® silica gel column (50 mm×250 mm), eluting with a mixture of methyl tert-butyl ether-hexane (40:60) at a flow rate of 85 mL/min. to yield the separated compounds A (0.2 g, 0.44 mmol, 15%) and B (0.16 g, 0.36 mmol, 12%);

Compound A: methyl 1-[3-chloro-4-(5H-pyrrolo[2,1-c][1,4]benzodiazepin-10(11H)-ylcarbonyl)phenyl]-1H-pyrazole-3-carboxylate, m.p. oil;

MS [(+APCI), m/z]: 447/449 [M+H]$^+$, contains one chlorine atom;

$^1$H NMR (400 MHz, CDCl$_3$) δ: 7.97 (d,, J=6.6 Hz, 1H, ArH-6), 7.85 (d, J=2.6 Hz, 1H, ArH"-5"-pyrazole), 7.70 (d, J=2.0 Hz, 1H, ArH'-3'), 7.46 (dd, J=8.3, 2.0 Hz, 1H, ArH'-5'), 7.24 (m, 2H, ArH-9, ArH'-6'), 7.08 (td, J=7.0, 2.2 Hz, 1H, ArH-8), 7.04 –7.00 (t, J=7.9 Hz, 1H, ArH-7), 6.97 (d, J=2.4 Hz, 1H, ArH"-4"), 6.68 (t, J=2.2 Hz, 1H, ArH-3), 6.09 (br s, 1H, ArH-1), 6.06 (dd, J=3.3, 2.9 Hz, 1H, ArH-2), 5.70–4.72 (broad, 4H, ArH-5,11), 3.95 (s, 3H, —OCH$_3$-3");

$^{13}$C NMR (100 MHz, CDCl$_3$) δ: 166.8 (s, 1C, —C(O)N—), 162.2 (s, 1C, —CO$_2$CH$_3$), 145.5 (s, 1C), 140.1 (s, 1C), 140.0 (s, 1C), 135.2 (s, 1C), 134.6 (s, 1C), 129.2 (s, 1C), 129.1 (s, 1C), 128.6 (s, 1C), 128.5 (s, 1C), 128.4 (s, 1C), 128.1 (s, 1C), 125.5 (s, 1C), 121.8 (s, 1C), 121.0 (s, 1C), 117.5 (s, 1C), 111.0 (s, 1C, ArC-3), 109.1 (s, 1C, ArC-1), 107.7 (s, 1C ArC-2), 107.0 (s, 1C, ArC-11a), 52.3 (s,1C, —OCH$_3$-3"), 51.0 (s, 1 C, ArC-5), 45.7 (s,1C, ArC-11);

Additional NMR experiments (NOE, COSY, HMBC) confirmed the structural assignments and chemical shifts.

Compound B: methyl 2-chloro-4-[3-(5H-pyrrolo[2,1-c][1,4]benzodiazepin-10(11H)-ylcarbonyl)-1H-pyrazol-1-yl]benzoate, m.p. 153–155;

MS [(+APCI), m/z]: 447/449 [M+H]$^+$, contains one chlorine atom;

IR (Solid), v$_{max}$: 1720, 1645, 1600, 1495, 1270, 1195, 775, 750, 725 cm$^{-1}$;

$^1$H NMR (400 MHz, CDCl$_3$) δ: 7.86 (d,, J=8.3 Hz, 1 H, ArH"-6"), 7.78 (br s,1H, ArH'-5'-pyrazole), 7.46 (dd, J=7.5, 1.3 Hz, 1 H, ArH-6), 7.34–7.23 (m, 4H, ArH-7,8, ArH"-3", 5"), 7.08 (d, J=6.8 Hz, 1H, ArH-9), 6.75 (br s,1H, ArH'-4'-pyrazole), 6.65 (t, J=2.2 Hz, 1H, ArH-3), 6.09 (dd, J=3.3, 2.9 Hz, 1H, ArH-2), 6.05 (brs, 1H, ArH-1), 3.93 (s, 3H, —OCH$_3$-1");

$^{13}$C NMR (100 MHz, CDCl$_3$) δ: 165.1 (s,1 C, —C(O)N—), 161.7 (s,1C, —CO$_2$CH$_3$), 148.5 (s, 1C), 143.4 (s, 1C), 142.0 (s, 1C), 135.4 (s, 1C), 132.8 (s,1C), 129.3 (s, 1C), 128.5 (s, 1C), 128.2 (s, 1C), 128.1 (s, 1C), 127.4 (s, 1C), 126.9 (s, 1C), 126.3 (s, 1C), 121.5 (s, 1C), 121.2 (s, 1C), 115.8 (s, 1C, ArC-1), 111.2(s, 1C, ArC-3), 107.7(s, 1C, ArC-2), 107.3 (s, 1C, ArC-11a), 52.5 (s, 1C, -OCH$_3$-3"), 51.4 (s,1C, ArC-5), 45.6 (s, 1C, ArC-11);

Additional NMR experiments (NOE, COSY, HMBC) confirmed the structural assignments and chemical shifts;

Anal. calcd for C$_{24}$H$_{19}$ClN$_4$O$_3$: C, 64.50; H, 4.29; N, 12.54. Found: C, 64.16; H, 3.95; N, 12.40.

Step c

{1-[3–Chloro-4-(5H-pyrrolo[2,1-c][1,4]benzodiazepin-10(11H)-ylcarbonyl)phenyl]-1H-pyrazol-3-yl}methanol A stirred solution of methyl 1-[3-chloro-4-(5H-pyrrolo[2,1-c][1,4]benzodiazepin-10(11H)-ylcarbonyl)phenyl]-1H-pyrazole-3-carboxylate (0.14 g, 0.31 mmol) in tetrahydrofuran (5 mL) was heated at reflux and treated with a solution of 2.0 M lithium borohydride in tetrahydrofuran (3 mL, 6.0 mmol) in three 1 mL aliquots over 1.5 hours. After cooling to room temperature, the reaction was quenched with 2 N hydrochloric acid, and extracted with ethyl acetate (3×). The combined organic phase was washed with water, dried over anhydrous sodium sulfate, filtered, and evaporated in vacuo to a residue. Trituration of the residue with a mixture of methyl tert-butyl ether and hexane afforded a white amorphous powder which was purified by preparative normal phase high-performance liquid chromatography on a Primesphere® silica gel column (50 mm×250 mm), eluting with 100% methyl tert-butyl ether at a flow rate of 70 mL/min. to yield, after evaporation of the solvent, the title compound (0.05 g, 0.11 mmol, 37%) as a colorless amorphous solid, m.p. 85° C.;

MS [(+APCI), m/z]: 419/421 [M+H]$^+$, contains one chlorine atom;

$^1$H NMR (400 MHz, CDCl$_3$) δ: 7.79 (d,, J=2.4 Hz, 1H, ArH"-5"-pyrazole), 7.62 (d, J=1.5 Hz, 1H, ArH'-3'), 7.60–7.30 (m, 1H, ArH-6), 7.39 (dd, J=8.3, 1.8 Hz, 1H, ArH'-5'), 7.24 (d, J=8.3 Hz, 1H, ArH'-6'), 7.19 (br d, 1H, ArH-9), 7.08 (td, J=7.5, 1.8 Hz, 1H, ArH-8), 7.00 (m, 1H, ArH-7), 6.68 (t, J=2.2 Hz, 1H, ArH-3), 6.44 (d, J=2.4 Hz, 1H, ArH"-4"-pyrazole), 6.09 (br s, 1H, ArH-1), 6.07 (dd, J=3.5, 2.6 Hz, 1H, ArH-2), 4.80–5.50 (broad m, 4H, 5 & 11 H), 4.74 (d, J=5.9 Hz, 2H, -CH$_2$OH), 1.96 (t, J=5.9 Hz, 1H, —OH);

$^{13}$C NMR (100 MHz, CDCl$_3$) δ: 167.1 (s, 1C, —C(O) N—), 154.7 (s, 1C), 140.6 (s, 1C), 140.3 (s, 1C), 134.6 (s, 1C), 133.7 (s, 1C), 132.4 (s, 1C), 129.8 (s, 1C), 129.2 (s, 1C), 129.1 (s, 1C), 128.6 (s, 1C), 127.9 (s, 1C), 127.8 (s, 1C), 125.6 (s, 1C), 121.7 (s, 1C), 119.7 (s, 1C), 116.2 (s, 1C), 109.1 (s, 1C, ArC-1), 107.7 (s, 1C, ArC-2), 107.0 (s, 1C, ArC-11a), 59.1 (s, 1C, —CH$_2$OH), 51.1 (s, 1 C, ArC-5), 45.7 (s, 1C, ArC-11);

Anal. calcd for C$_{23}$H$_{19}$ClN$_4$O$_2$: C, 65.95; H, 4.57; N, 13.38. Found: C, 65.69; H, 4.97; N, 12.58.

The invention claimed is:

1. A compound of Formula (I)

Formula (I)

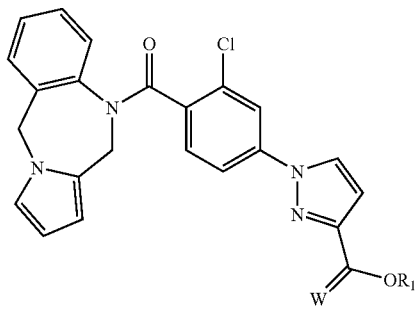

wherein

W represents either a double-bonded O or two single bonded H;

R$_1$ is selected from the group consisting of R, R$_3$—X—R$_2$—, R$_3$—S(O)—, R$_3$—S(O)$_2$—, —SO$_3$R$_4$, —S(O)$_2$N(R)$_2$, and D-glucuronide, when W is hydrogen, or R$_1$ is selected from the group consisting of hydrogen, alkyl, cycloalkyl, aryl, arylalkyl, heteroaryl, and heteroarylalkyl, when W is oxygen;

R$_2$ is selected from the group consisting of alkylene, cycloalkylene, alkylene-X-alkylene, alkylene-X-cycloalkylene, cycloalkylene-X-alkylene, and cycloalkylene-X-cycloalkylene;

R$_3$ is selected from the group consisting of alkyl, aryl, heteroaryl, cycloalkyl, alkenyl, cycloalkenyl, alkynyl, alkenyl-X-alkylene, cycloalkenyl-X-alkylene, and perfluoroalkyl;

R$_4$ is selected from the group consisting of hydrogen and R3;

R is independently selected from the group consisting of hydrogen, alkyl, alkenyl, alkynyl, cycloalkyl, cycloalkenyl, monofluoroalkyl, perfluoroalkyl, aryl, arylalkyl, heteroaryl, heteroarylalkyl, hydroxyl-(C$_1$–C$_6$)alkyl, alkoxyalkyl, alkylthioalkyl, acyl, alkoxycarbonyl, —C(O)NH2, alkylaminocarbonyl, dialkylaminocarbonyl, alkylaminoalkyl, and dialkylaminoalkyl, and when two R groups are bonded to the same atom the two R groups together may form an alkylene group;

X is selected from the group consisting of oxygen, —NR—, —S(O)m-,—C(O)—, —OC(O)—, —C(O) O—, —NRC(O)—, and —C(O)NR—; and m is an integer selected from 0, 1, and 2, and the racemates, enantiomers, and pharmaceutically acceptable salts thereof.

2. The compound of claim 1 wherein W is O.

3. The compound of claim 1 of the formula

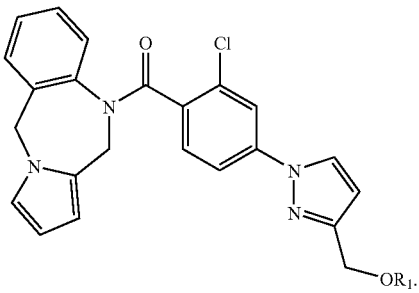

4. The compound according to claim 1, which is (1-[3-chloro-4-(5H-pyrrolo[2,1-c][1,4]benzodiazapin-10(11 H)-ylcarbonyl)phenyl]-1 H-pyrazol-3-yl)methanol.

5. A pharmaceutical composition comprising a pharmaceutically effective amount of the compound of claim 1 and a pharmaceutically acceptable carrier.

6. The pharmaceutical composition according to claim 5 wherein the compound is (1-[3-chloro-4-(5H-pyrrolo [2,1-c][1,4]benzodiazapin-10(11 H)-ylcarbonyl)phenyl[-1 H-pyrazol-3-yl)methanol.

7. The composition of claim 5 wherein said carrier is a solid.

8. The composition of claim 5 wherein said carrier is a liquid.

9. A method of treating nocturnal enuresis, nocturia or urinary incontinence comprising administering to a patient in need thereof an effective amount of the compound of claim 1.

10. The method of claim 9 wherein said compound is (1-[3-chloro-4-(5H-pyrrolo [2,1-c][1,4]benzodiazapin-10 (11 H)-ylcarbonyl)phenyl]-1 H-pyrazol-3-yl)methanol.

11. A process for making the compound of claim 1 comprising reacting an ester compound of formula

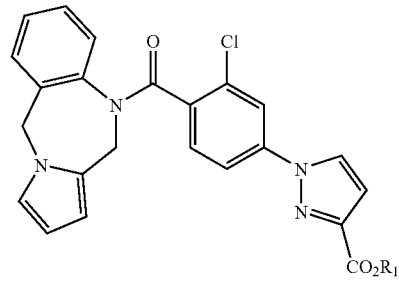

wherein R$_1$ is as defined in claim 1, with an excess of a borohydride reducing agent in a suitable solvent to produce an alcohol compound of formula

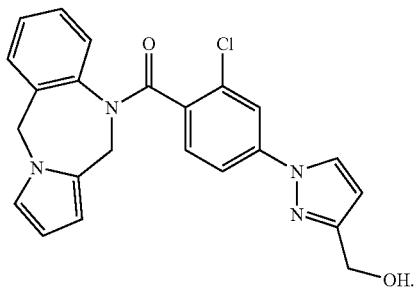

12. A process according to claim 11 further comprising reacting the alcohol compound with a compound of formula $R_1$-Z and a suitable base in a suitable solvent to produce an alkylated or acylated compound

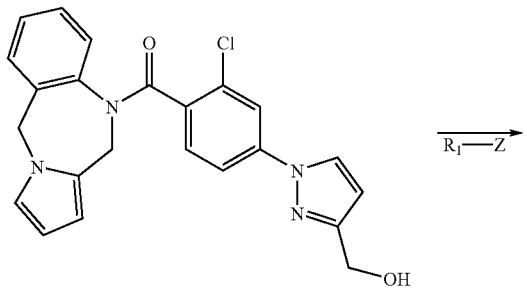

$\xrightarrow{R_1-Z}$

-continued

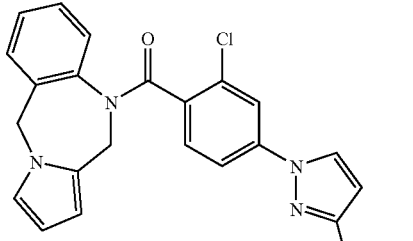

wherein $R_1$ is selected from the group consisting of R, $R_3$—X—$R_2$—, $R_3$—S(O)—, $R_3$—S(O)$_2$—, —SO$_3$R$_4$, —S(O)$_2$N(R)$_2$, and D-glucuronide, when W is hydrogen, or $R_1$ is selected from the group consisting of hydrogen, alkyl, cycloalkyl, aryl, arylalkyl, heteroaryl, and heteroarylalkyl, when W is oxygen, and Z is a leaving group selected from the group consisting of chloro, bromo, iodo, —OSO$_2$CF$_3$, and hydroxy.

* * * * *